(12) United States Patent
Zou et al.

(10) Patent No.: US 8,961,498 B2
(45) Date of Patent: Feb. 24, 2015

(54) ELECTRONIC PILL COMPRISING A PLURALITY OF MEDICINE RESERVOIRS

(75) Inventors: Hans Zou, Windsor, NJ (US); Jeff Shimizu, Cortlandt Manor, NY (US); Lucian R. Albu, Forrest Hills, NY (US); Johan F. Dijksman, Eindhoven (NL)

(73) Assignee: Medimetrics Personalized Drug Delivery, Eindhoven (NL)

( * ) Notice: Subject to any disclaimer, the term of this patent is extended or adjusted under 35 U.S.C. 154(b) by 876 days.

(21) Appl. No.: 12/992,613

(22) PCT Filed: Jun. 18, 2009

(86) PCT No.: PCT/IB2009/052604
§ 371 (c)(1),
(2), (4) Date: Jan. 11, 2011

(87) PCT Pub. No.: WO2009/156919
PCT Pub. Date: Dec. 30, 2009

(65) Prior Publication Data
US 2011/0092959 A1    Apr. 21, 2011

Related U.S. Application Data

(60) Provisional application No. 61/075,499, filed on Jun. 25, 2008.

(51) Int. Cl.
*A61K 9/22*    (2006.01)
*A61K 9/20*    (2006.01)
(Continued)

(52) U.S. Cl.
CPC ..................... *A61M 31/002* (2013.01)
USPC .......................... 604/890.1; 604/135; 424/464

(58) Field of Classification Search
CPC .................................................. A61M 31/002

USPC ........ 604/890.1, 891.1, 892.1, 500, 503, 504, 604/505, 514, 516, 64, 134, 135; 424/451, 424/457, 464, 468
See application file for complete search history.

(56) References Cited

U.S. PATENT DOCUMENTS 3,693,027 A * 9/1972 Garaway ........................... 361/5
4,102,998 A   7/1978 Gutnick
(Continued)

FOREIGN PATENT DOCUMENTS

CN    1958090    5/2007
DE    3339323    5/1985
(Continued)

OTHER PUBLICATIONS

Translated Chinese Office Action mailed Aug. 5, 2013 for Chinese patent application No. 201080015953.5, a counterpart foreign application of U.S. Appl. No. 13/262,841, 7 pages.
(Continued)

*Primary Examiner* — Andrew Gilbert
(74) *Attorney, Agent, or Firm* — Lee & Hayes, PLLC

(57) ABSTRACT

Electronic pill (1, 11, 21) comprising a plurality of medicine reservoirs (2, 12, 22), each of the reservoirs comprising a discharge opening (3, 13, 23) covered by a removable cover (6, 16, 26). The pill comprises at least one actuator responsive to control circuitry for removing the cover from the discharge opening (3, 13, 23). The actuator can for example be a spring loaded piston (4) breaking a foil cover when dispensing the medicament. 5 Alternatively, the cover can be a rotatable disk (16) or cylinder (26) with an opening (17, 27) which can be brought in line with the discharge opening of a reservoir under the action of the actuator.

15 Claims, 3 Drawing Sheets

(51) Int. Cl.
*A61M 5/20* (2006.01)
*A61M 31/00* (2006.01)

(56) References Cited

U.S. PATENT DOCUMENTS

| | | | |
|---|---|---|---|
| 4,564,363 A * | 1/1986 | Bagnall et al. | 604/891.1 |
| 4,572,403 A | 2/1986 | Benaroya | |
| 4,814,180 A | 3/1989 | Eckenhoff et al. | |
| 5,167,625 A * | 12/1992 | Jacobsen et al. | 604/891.1 |
| 5,167,626 A * | 12/1992 | Casper et al. | 604/891.1 |
| 5,279,607 A | 1/1994 | Schentag et al. | |
| 5,318,557 A | 6/1994 | Gross | |
| 5,567,592 A | 10/1996 | Benet et al. | |
| 5,728,396 A | 3/1998 | Peery et al. | |
| 6,010,492 A * | 1/2000 | Jacobsen et al. | 604/503 |
| 6,349,232 B1 * | 2/2002 | Gordon | 604/20 |
| 6,803,373 B2 | 10/2004 | Schellens | |
| 6,902,544 B2 * | 6/2005 | Ludin et al. | 604/93.01 |
| 7,030,132 B2 | 4/2006 | Schellens et al. | |
| 8,333,754 B2 * | 12/2012 | Boyden et al. | 604/891.1 |
| 2002/0072735 A1 | 6/2002 | Kupperblatt et al. | |
| 2003/0020810 A1 | 1/2003 | Takizawa et al. | |
| 2003/0213495 A1 | 11/2003 | Fujita et al. | |
| 2004/0242962 A1 | 12/2004 | Uchiyama | |
| 2004/0253304 A1* | 12/2004 | Gross et al. | 424/451 |
| 2004/0267241 A1 | 12/2004 | Russell | |
| 2005/0147559 A1 | 7/2005 | von Alten | |
| 2005/0158246 A1* | 7/2005 | Takizawa et al. | 424/10.1 |
| 2006/0145876 A1 | 7/2006 | Kimura et al. | |
| 2006/0155174 A1 | 7/2006 | Glukhovsky et al. | |
| 2007/0138027 A1 | 6/2007 | Dinsmoor et al. | |
| 2007/0213659 A1* | 9/2007 | Trovato et al. | 604/67 |
| 2009/0306633 A1* | 12/2009 | Trovato et al. | 604/891.1 |
| 2010/0063485 A1* | 3/2010 | Johnson et al. | 604/890.1 |
| 2010/0280464 A1 | 11/2010 | De Graaff et al. | |

FOREIGN PATENT DOCUMENTS

| | | |
|---|---|---|
| FR | 2794654 | 12/2000 |
| JP | 2002532162 | 10/2002 |
| JP | 2003520108 | 7/2003 |
| JP | 2005511184 | 4/2005 |
| WO | WO03008637 | 1/2003 |
| WO | WO03068061 | 8/2003 |
| WO | WO2005025647 | 3/2005 |
| WO | WO2005038049 | 4/2005 |
| WO | WO2006021932 | 3/2006 |
| WO | WO2006025013 | 3/2006 |
| WO | WO2006044049 | 4/2006 |
| WO | WO2006056944 | 6/2006 |
| WO | WO2006077529 | 7/2006 |
| WO | WO2008029372 | 3/2008 |
| WO | WO2008038199 | 4/2008 |
| WO | WO2008062335 | 5/2008 |
| WO | WO2010086681 | 8/2010 |

OTHER PUBLICATIONS

European Office Action mailed Jul. 25, 2013 for European patent application No. 10779040.4, a counterpart foreign application of U.S. Appl. No. 13/498,835, 4 pages.

Japanese Office Action mailed Jun. 25, 2013 for Japanese patent application No. 2012531527, a counterpart foreign application of U.S. Appl. No. 13/498,835, 8 pages.

Office action for U.S. Appl. No. 13/262,861, mailed on Aug. 2, 2013, Shimizu et al., "Valveless Drug Delivery Device ", 8 pages.

Chinese Office Action mailed Jan. 15, 2013 for Chinese patent application No. 201080015953.5, a counterpart foreign application of U.S. Appl. No. 13/262,841, 17 pages.

Chinese Office Action mailed Jan. 21, 2013 for Chinese patent application No. 201080040663.6, a counterpart foreign application of U.S. Appl. No. 13/390,111, 8 pages.

Chinese Office Action mailed Mar. 14, 2013 for Chinese patent application No. 200980112018.8, a counterpart foreign application of U.S. Appl. No. 12/933,891, 12 pages.

Chinese Office Action mailed May 13, 2013 for Chinese patent application No. 201080015284.1, a counterpart foreign application of U.S. Appl. No. 13/262,861, 11 pages.

Evans, et al., "Measurement of Gastrointestinal pH Profiles in Normal Ambulant Human Subjects", Gut, vol. 29, 1988, pp. 1035-1041.

Japanese Office Action mailed Apr. 16, 2013 for Japanese Patent Applicaiton No. 2011-514179, a counterpart foreign application of U.S. Appl. No. 12/992,305, 9 pages.

Japanese Office Action mailed Apr. 30, 2013 for Japanese patent application No. 2010-546431, a counterpart foreign application of U.S. Appl. No. 12/867,888, 4 pages.

Kompella, et al., "Delivery System for Penetration Enhancement of Peptide and Protein Drugs: Design Considerations", Advanced Drug Delivery Reviews, vol. 46, 2001, pp. 211-245.

Paine, et al., "Characterization of Interintestinal and Intraintestinal Variations in Human CYP3A-Dependent Metabolism", The Journal of Pharmacology and Experimental Therapeutics, vol. 283, No. 3, 1997, pp. 1552-1562.

Siccardi, et al., "Regulation of Intestinal Epithelial Function: A Link Between Opportunities for Macromolecular Drug Delivery and Inflammatory Bowel Disease", Advanced Drug Delivery Reviews, vol. 57, 2005, pp. 219-235.

* cited by examiner

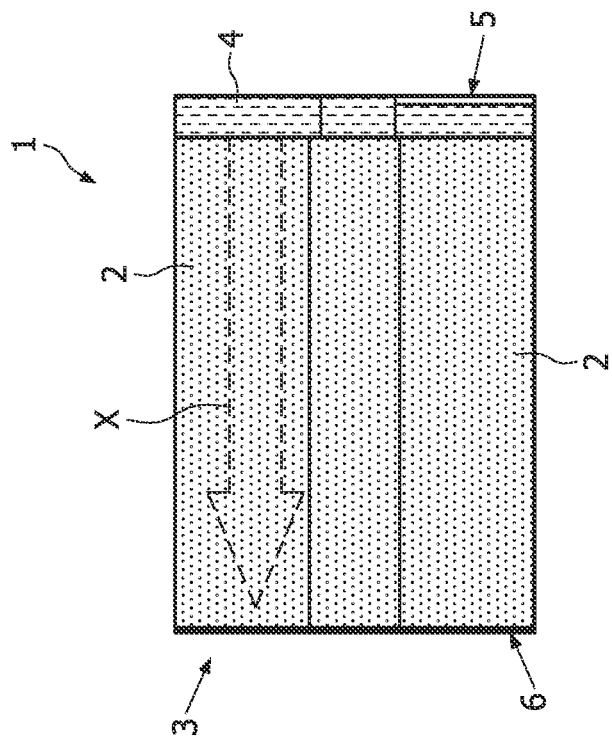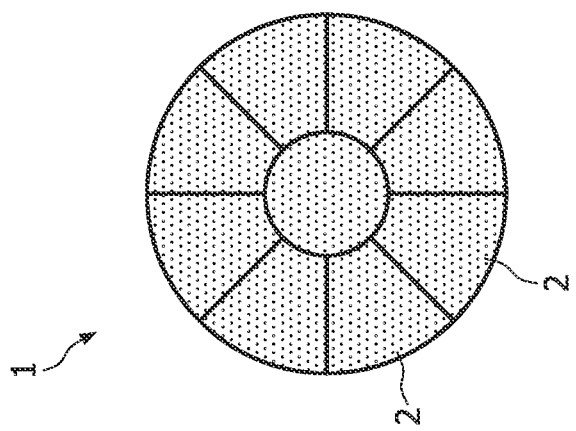

ELECTRONIC PILL COMPRISING A PLURALITY OF MEDICINE RESERVOIRS

CROSS REFERENCE TO RELATED CASES

Applicants claim the benefit of International Application Number PCT/IB2009/052604, filed Jun. 18, 2009, and Provisional Application Ser. No. 61/075,499, filed Jun. 25, 2008.

FIELD OF THE INVENTION

The present invention relates to an electronic pill comprising a plurality of medicine reservoirs for targeted drug delivery while passing the gastro-intestinal tract. The invention also relates to a method for preparing such an electronic pill.

BACKGROUND OF THE INVENTION

Electronic pills are electronically controlled ingestible capsules which can be used to provide therapeutic treatment during traversal of the alimentary tract. An electronic pill generally comprises a medicine reservoir, a dispensing opening, and a pump for transporting the medicine from the reservoir to the dispensing opening. Generally, the electronic pill also comprises control means to activate the dispensing pump at the desired moment, e.g. responsive to a signal from a sensor, such as a pH sensor which can be an integral part of the pill. After swallowing the pill is moved along the alimentary tract by the peristaltic movement of the muscles along the alimentary tract. During its travel through the intestines the pill drifts from the pylorus to the ileocaecal valve at about 1 m/hour. Due to the peristalsis of the small intestines superposed on the drift velocity, large velocity variations occur pushing the pill back and forth through the intestines. This way medication released from the pill is mixed thoroughly before it will be taken up through the wall of the intestines or becomes locally effective.

An example of an electronic pill is disclosed in WO 2006077529. One of the embodiments of the electronic pill disclosed in this publication comprises different reservoirs for delivering more than one medicament. Associated closure members are independently controlled for dispensing medicament.

Being capable of dispensing a medical fluid is useful for medicines which are in liquid form, or aqueous solution or suspension. However, a majority of drugs are in solid state and have poor solubility in a biocompatible solvent and often their solutions have a much shorter shelf life (typically factor 1000 shorter than solid) as compared with solid. Powder or granule is a common elemental or intermediate form of in the production of a drug. It is therefore very desirable to have an electronic capsule capable of dispensing medication powders or granules.

Powder dispensers have been used widely in various industries, such as the pharmaceutical industry where they are used as in-line dosing, handling, or transport equipment. When these powder dispensers are in operation, they are in a fixed orientation, may use a gravity feed, and are continuously fed with powder supply. Further, they always dispense powders in air. A powder dispenser to be used in an electronic capsule must release powder in a wet environment, even under a fluid, and can not assume a dominant orientation. Because of these unconventional conditions, existing powder dispensers are not suitable for an electronic capsule to release medication powders. The wet environment presents another problem for some moisture-absorbing powders, which may crystallize or cluster quickly after absorbing moisture. Another limitation is presented by large particle size distribution, which makes precise dosing difficult with a miniaturized powder dispenser based on continuous feeding. For both research and therapy, it is desirable to delivery drugs as powder in given doses to multiple targeted locations of the gastro-intestinal tract autonomously.

SUMMARY OF THE INVENTION

It is an object of the present invention to provide a solution to deliver medication including powders of different properties (particle size distribution, cohesiveness, moisture absorption, etc.) in multiple doses to multiple targeted locations in the gastrointestinal tract with a single ingestible electronic capsule.

The object of the invention is achieved with an electronic pill comprising a plurality of medicine reservoirs, each of the reservoirs comprising a discharge opening covered by a removable cover, the pill comprising at least one actuator responsive to control circuitry for removing the cover from the discharge opening. This way, it is made possible to separately store quantities of one or more medicament and to release the medicine in a reservoir in one shot according to a pre-programmed sequence. Release from each reservoir can be kept independent from the other reservoirs. Medication in each reservoir can be effectively protected against exposure to moisture until being dispensed. The one or more actuators can be controlled by control circuitry, such as a programmable microprocessor in the pill, which can be powered by an energy source, such as a battery, within the pill.

In a particular embodiment, one or more of the medicament reservoirs can comprise an actuator, the actuators of the respective reservoirs being mutually independently responsive to control circuitry for displacing medicine from the reservoir to the discharge opening, while the discharge opening is sealed by a sealing foil breakable under the action of the corresponding actuator. Such a breakable cover can for example be made of a breakable biocompatible foil.

Suitable actuators are for example spring loaded pistons. Other suitable types are actuators triggered by a memory alloy, e.g., deformable under the influence of temperature. Further suitable actuators are actuators triggered by a fuse breakable under the action of an applied electric current.

Alternatively, the cover can be a rotatable, or translatable, disk with an opening which can selectively be brought in line with the discharge opening of each of the reservoirs under the action of the actuator. This way, the reservoirs can be opened one by one to release the contained medicine. The disk can be rotated under the control of the control circuitry of the electronic pill. The actuator can for example be a spiral spring element acting on the rotatable member to move it by discrete steps. With each subsequent discrete step, the opening in the disk is in line with the discharge opening of a single reservoir.

The disk can be extended to a rotatable tube or cylinder with an open slot in the cylinder outer wall. Each of the reservoirs is opened when the slot is brought in line with the discharge opening for selectively dispensing the medicament. Since each reservoir is opened actively and the opening is large enough, no additional piston is needed to release the medicament.

The reservoirs can have any suitable shape. They can for example be longitudinal, e.g., tubular, reservoirs with parallel longitudinal axes and having a cross section corresponding to the outline of the discharge opening. Optionally, the reservoirs are formed as adjacent radial cylinder sections.

The object of the invention is further achieved by a method for preparing an electronic pill comprising the steps of:

providing an electronic pill having a plurality of medicine reservoirs, each of the reservoirs comprising a discharge opening;

filling each of the reservoirs with a medicine in quantities corresponding to predefined dosage regime;

covering the discharge openings with a cover releasable under the action of an actuator.

The cover can for example be released by rotating or sliding it to a position where it leaves open the discharge opening of a selected medicament reservoir. Alternatively, the cover can be a breakable seal breakable under the action of an actuator within the medicament reservoir, such as a piston pushing the medicament out off the reservoir.

BRIEF DESCRIPTION OF THE DRAWINGS

The present invention will be elucidated with reference to the drawings wherein:

FIG. 1A shows in plan view a medicament reservoir of an electronic pill according to the present invention;

FIG. 1B shows in longitudinal cross section the reservoir of FIG. 1A;

FIGS. 1A and 1B show schematically an electronic pill 1 comprising multiple longitudinal medicament reservoirs 2 each having a discharge opening 3 at one end. The discharge opening 3 corresponds to the cross section of the respective reservoir 2. In each reservoir 2 there is a slideable piston 4 which is kept constrained at the end 5 opposite the discharge opening 3 by a mechanical trigger (not shown). After medication is loaded into each of the reservoirs 2, a sealing cover 6 is applied over each discharge opening 3. When medication in one reservoir 2 is going to be released, a command is sent from a microprocessor (not shown) within the electronic pill 1 to activate the trigger and as a result the piston 4 slides quickly toward the discharge opening 3 of the corresponding reservoir 2, breaking the sealing cover 6 and pushing all medication out of the reservoir 2 in a single shot.

The pistons 4 are spring loaded so that they can move under the spring force to push medication out of the corresponding reservoir 2. The spring can be located in de medicine reservoir 2 opposite the discharge opening 3. Other suitable actuators can comprise a memory alloy, e.g., deformable under the influence of temperature, or actuators triggered by a fuse breakable under the action of an applied electric current.

The sealing cover 6 is made of a biocompatible plastic film, which is breakable under the pushing action of the actuator.

For a high transportation efficiency and to minimize friction the reservoir surface can be properly treated, for example it can be coated with a non-stick coating, such as a silicon based and/or fluoropolymer based coating.

To ease breaking of said sealing cover 6, some features to weaken tear strength may be created on the sealing cover 6, for example, uneven thickness distribution.

Figure 2:
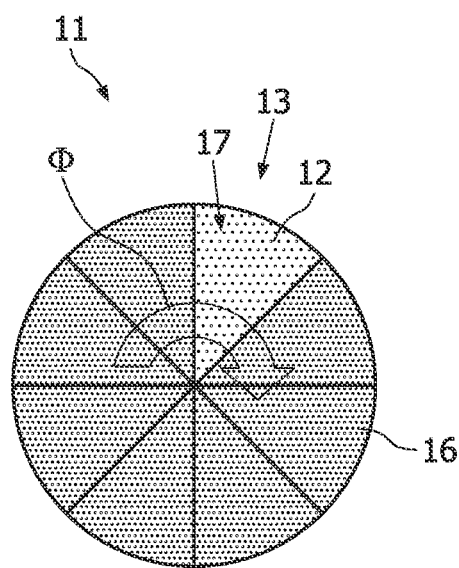
FIG. 2 shows in plan view a medicament reservoir of an electronic pill according to the present invention.

FIG. 2 shows an electronic pill 11 comprising multiple medicament reservoirs 12. The reservoirs 12 have a cross-section in the shape of a circle segment, together forming a circular cross section. The reservoirs 12 have adjacent discharge openings 13 covered by a rotatable disk 16. The rotatable disk 16 is provided with an opening 17 with the same shape and size as the discharge openings 13 of the reservoirs 12. When medication in one of the reservoirs 12 is released, the reservoir 12 is opened by rotating the disk 16 until the opening 17 is in line with the discharge opening 13 of the reservoir 12. This way, the reservoirs are opened one by one according to a predetermined medicament delivery program.

Figure 3:
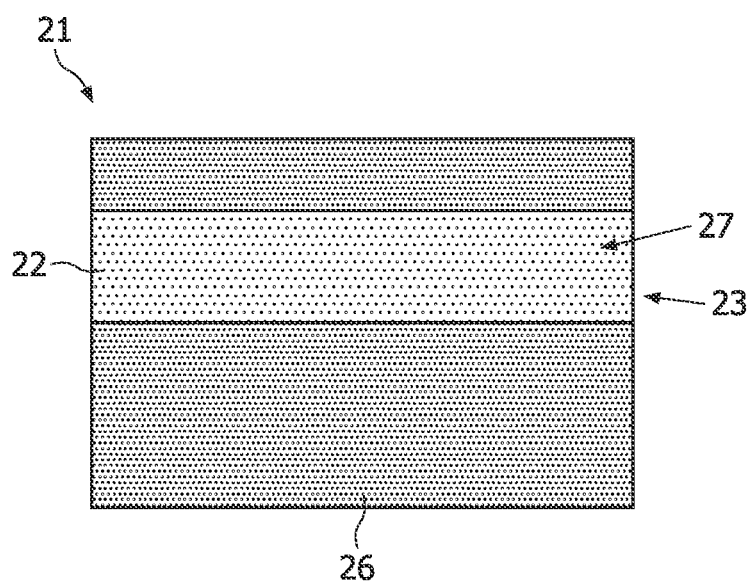
FIG. 3 shows in longitudinal cross section the reservoir of a further alternative embodiment of the pill according to the invention.

FIG. 3 shows an alternative electronic pill 21, where the rotatable disk is replaced by a rotatable tube or cylinder wall 26 with a slot 27. Each of the reservoirs 22 has a slot shaped discharge opening 23 parallel to the slot 27. This way, slot 27 can be brought in line with the respective slots 23, as shown in the drawing, for selectively opening the medicament reservoirs 22 and releasing the contained medicament.

The rotatable tube 26 or disk 16 can for example be driven by a spiral spring (not shown) and the medicament can be released at discrete steps so that each rotation-step opens one single reservoir 22 at the time. It can also be envisioned that the rotatable tube 26 or disk 16 are combined to open a reservoir at two sides simultaneously to accelerate medication spreading at the target.

Figure 4:
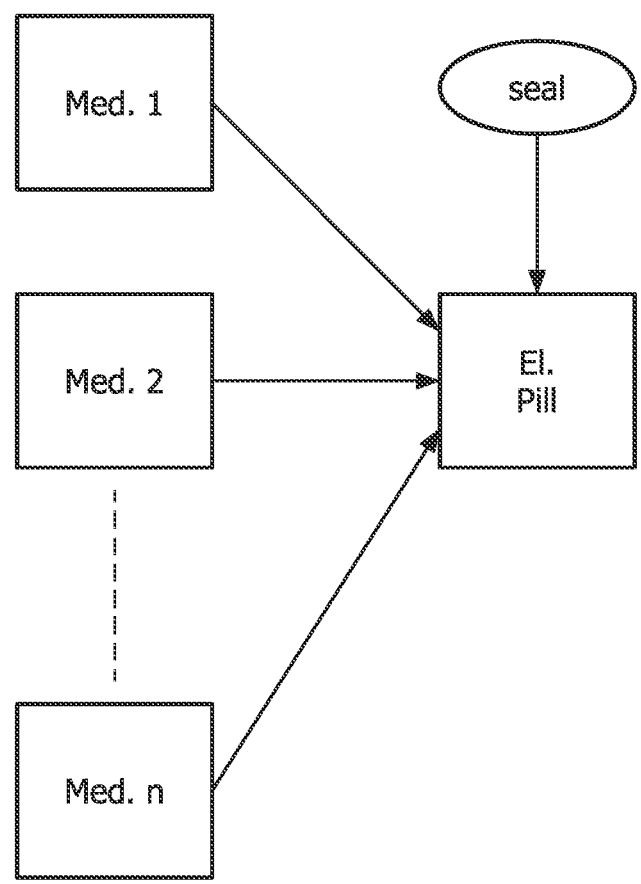
FIG. 4 shows a flow chart schematically representing the method according to the invention.

FIG. 4 shows a flow chart representing the method according to the present invention. An electronic pill comprises a plurality of medicine reservoirs, as described above, which are filled with medicines (Med. 1, Med. 2 up to Med. N in FIG. 4) in quantities corresponding to predefined dosage regime. Subsequently, the discharge openings are sealed with a seal cover releasable under the action of an actuator, as described for the embodiments above.

To ensure isolation of medication from environmental moisture or cross-contamination, each reservoir 12, 22 may be sealed with a soft film after loading medication. Rotating the disk 16 or tube 26 involves peeling off the film from the discharge opening of the reservoir.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An electronic pill comprising:
a plurality of medicine reservoirs, each of the plurality of medicine reservoirs comprising a discharge opening covered by a removable cover;
a plurality of mechanical actuators, each of the plurality of mechanical actuators corresponding to each of the plurality of medicine reservoirs, each of the plurality of mechanical actuators configured to increase a pressure in the corresponding medicine reservoir to force contents contained in the corresponding medicine reservoir out of the respective medicine reservoir, through the respective discharge opening, wherein the removable cover comprises a rotatable member with an opening which can selectively be brought in line with the discharge opening of each of the plurality of medicine reservoirs under the action of an actuator.

2. The electronic pill according to claim 1 wherein the removable cover further comprises a film removable by rotation of the rotatable member.

3. The electronic pill according to claim 1 wherein the actuator is a spiral spring element acting on the rotatable member to move it by discrete steps to bring the opening in the rotatable member in line with a single reservoir with each subsequent discrete step.

4. The electronic pill according to claim 1 wherein the rotatable member comprises a disk having an opening which can be brought in line with the respective discharge opening of each of the plurality of medicine reservoirs.

5. The electronic pill according to claim 1 wherein each of the plurality of mechanical actuators comprises a spring loadable piston in at least a part of the respective medicine reservoir.

6. The electronic pill according to claim 1 wherein each of the plurality of mechanical actuators comprises a memory alloy in at least a part of respective medicine reservoir.

7. The electronic pill according to claim 1 wherein each of the plurality of mechanical actuators comprises a fuse breakable under the action of an applied electric current in at least a part of respective medicine reservoir.

8. The electronic pill according to claim 1 wherein the plurality of medicine reservoirs are longitudinal reservoirs with parallel longitudinal axes and having a cross section corresponding to the discharge opening.

9. The electronic pill according to claim 1 wherein the plurality of medicine reservoirs form adjacent radial cylinder sections.

10. The electronic pill according to claim 3 wherein the rotatable member comprises a disk having an opening which can be brought in line with the respective discharge opening of each of the plurality of medicine reservoirs.

11. An electronic pill comprising:
a plurality of medicine reservoirs, each of the plurality of medicine reservoirs comprising a discharge opening;
a cover comprising a rotatable member with an opening, the cover being movable by an actuator to selectively place the opening in line with the discharge opening of each of the plurality of medicine reservoirs.

12. The electronic pill according to claim 11 wherein the actuator is a spiral spring element acting on the rotatable member to move it by discrete steps to bring the opening in the rotatable member in line with a single reservoir with each subsequent discrete step.

13. The electronic pill according to claim 12 wherein the rotatable member comprises a disk having an opening which can be brought in line with the respective discharge opening of each of the plurality of medicine reservoirs.

14. The electronic pill according to claim 11 wherein the rotatable member comprises a cylindrical wall enveloping the reservoirs and having a slot-shaped opening which can be brought in line with the respective discharge opening of each of the plurality of medicine reservoirs.

15. The electronic pill according to claim 11 wherein the rotatable member comprises a disk having an opening which can be brought in line with the respective discharge opening of each of the plurality of medicine reservoirs.

\* \* \* \* \*